US012064592B2

(12) United States Patent
Streit et al.

(10) Patent No.: US 12,064,592 B2
(45) Date of Patent: Aug. 20, 2024

(54) FIXATION OF RESERVOIR OF DRUG DELIVERY DEVICE

(71) Applicant: TecMed AG, Burgdorf (CH)

(72) Inventors: Ursina Streit, Kirchberg (CH); Roland Margot, Worb (CH); Jan Baumert, Grünen (CH); Simon Bosshard, Hindelbank (CH); Michael Hanimann, Bern (CH)

(73) Assignee: TecMed AG, Burgdorf (CH)

( * ) Notice: Subject to any disclaimer, the term of this patent is extended or adjusted under 35 U.S.C. 154(b) by 542 days.

(21) Appl. No.: 17/460,594

(22) Filed: Aug. 30, 2021

(65) Prior Publication Data

US 2022/0062537 A1 Mar. 3, 2022

(30) Foreign Application Priority Data

Sep. 1, 2020 (EP) .................................... 20193819

(51) Int. Cl.
*A61M 5/142* (2006.01)
*A61M 5/145* (2006.01)

(52) U.S. Cl.
CPC ...... *A61M 5/14244* (2013.01); *A61M 5/1452* (2013.01); *A61M 2205/0216* (2013.01)

(58) Field of Classification Search
CPC .... A61M 2005/14268; A61M 5/14244; A61M 5/14248; A61M 2005/2414; A61M 2205/0216; A61M 5/1452
See application file for complete search history.

(56) References Cited

U.S. PATENT DOCUMENTS

| 9,149,580 | B2 | 10/2015 | Jugl et al. | |
| 9,498,570 | B2* | 11/2016 | Cowan | A61M 5/31 |
| 2013/0006213 | A1* | 1/2013 | Arnitz | A61M 5/20 |
| | | | | 604/414 |

FOREIGN PATENT DOCUMENTS

| EP | 3257533 A1 | 12/2017 |
| EP | 3277345 A1 | 2/2018 |

* cited by examiner

*Primary Examiner* — Quynh-Nhu H. Vu
(74) *Attorney, Agent, or Firm* — Dorsey & Whitney LLP

(57) ABSTRACT

A module for a drug delivery device includes a first housing portion with a bearing element for supporting a neck or head portion of a first end of a reservoir and a second housing portion with an elastic contact element for supporting a second end of the reservoir opposite the first end. The first and second housing portions are configured to couple to each other in an assembled state in which the first and second housing portions form a cavity for accommodating the reservoir. The bearing element and the elastic contact element may each define a limiter or limiting structure of the cavity in a longitudinal direction of the cavity to secure or hold the reservoir free of play within the cavity. The elastic contact element may be is injection molded onto a surface of a body of the second housing portion.

20 Claims, 2 Drawing Sheets

FIXATION OF RESERVOIR OF DRUG DELIVERY DEVICE

CROSS-REFERENCE TO RELATED APPLICATIONS

This application claims priority to European Patent Application No. 20193819.8, filed Sep. 1, 2020, entitled "FIXATION OF RESERVOIR OF DRUG DELIVERY DEVICE," which is incorporated by reference herein, in its entirety and for all purposes.

TECHNICAL FIELD

Implementations relate to drug delivery devices for infusing, injecting, delivering, administering or dispensing substances and/or liquids such as insulin or hormone preparations, and more particularly provides a drug delivery device with two housing portions connectable to each other to hold a reservoir with the substance within the housing.

BACKGROUND

There are several solutions known in the art for holding a reservoir or cartridge within a drug delivery device, for example, within an infusion drug pump or within a cartridge holder of an injection pen.

For a precise setting and dispensing of a dose of a medication it is crucial that the reservoir is reliably held within the drug delivery device. Any movement of the reservoir relative to the housing of the drug delivery device needs to be prevented. If the reservoir were shifted within the drug delivery device, such as in a dose dispensing direction, the plunger within the reservoir would not be moved according to the set dose. If, for example, the reservoir is not fixed relative to the housing it may be shifted together with the plunger in the dispensing direction and thus the plunger within the reservoir is not moved according to the desired dosage. In this case, the dose dispensed out of the reservoir does not correspond to the dose set. Such inaccuracy may lead to an underdosing or overdosing, which can have serious consequences for the user.

For holding the reservoir non-movably within the delivery device, or within a reservoir holder attached to the delivery device, prior art approaches use elastic elements such as mechanical springs or deformable rubber or elastomer elements, which are arranged on one or both supporting ends of the reservoir. These elastic elements are intended to compensate for mechanical tolerances such that the reservoir can be fixed within the housing to prevent movement or play of the reservoir.

U.S. Pat. No. 9,149,580, for example, discloses a cartridge holder comprising a compression spring positioned at a shoulder portion of a cartridge. The compression spring absorbs an initially applied injection force acting on a piston and therefore on the cartridge. The cartridge holder is further equipped with a counter-bearing element adapted to provide a proximal end stop for the cartridge. Therefore, the cartridge is clamped between the counter-bearing element and the compression spring.

EP3257533 discloses an infusion pump comprising a reservoir within a housing of the pump. The retention of the reservoir within the housing is ensured in that a collar-shaped projection of a neck part of the housing rests on a tapered portion of the reservoir thereby pushing the reservoir against an internal flange of the housing.

EP3277345 discloses a cartridge holder comprising, on a needle side portion, axial ribs, which are plastically deformed against a cartridge neck portion when inserting the cartridge in the cartridge holder. At a proximal end of the cartridge holder a proximal support structure is connected to the cartridge holder and comprises proximal holding ribs adapted to engage a cartridge rim portion and to support the cartridge against movement in the proximal direction. The proximal ribs are not plastically deformable but are elastically deformable when mounting the cartridge into the cartridge holder.

SUMMARY

It is an objective of the present disclosure to simplify mounting of a reservoir within a drug delivery device and to reliably prevent a movement of the reservoir in a dispensing direction during drug dispensing.

This objective may be achieved by providing a housing of a drug delivery device, or of a disposable module of the drug delivery device, adapted to accommodate a reservoir for holding a liquid drug according to the implementations provided herein.

According to implementations, a module may include a first housing portion, which may include a rigid bearing element configured for supporting a neck or head portion of the reservoir, and a second housing portion, which may include an elastic contact element for supporting an end of the reservoir, which may be arranged opposite the neck or head portion of the reservoir. The first and second housing portions may be non-releasably or releasably connectable to each other to reach an assembled state in which the first and second housing portions may form a cavity, space or recess for accommodating the reservoir. The bearing element and the elastic contact element may each define a limiter or limiting structure of the cavity in a longitudinal direction of the cavity, together which may be configured to hold or support the reservoir and may prevent the reservoir from movement, or the reservoir may be free of play, within the cavity such that the reservoir may not move during dose setting and dose dispensing relative to the housing of the drug delivery device. According to implementations, the elastic contact element may be injection molded onto a surface of a body of the second housing portion (e.g., a two-component technique). The material of the elastic contact element may differ from the material of the body.

The elasticity of the elastic contact element may enable the elastic contact element to be compressed, for instance in the longitudinal direction of the cavity. This may enable the elastic contact element to compensate for a change in the length in the longitudinal direction between the rigid bearing element of the first housing portion and an inner surface of the second housing portion. For instance, in the assembled state, the distance in the longitudinal direction between the bearing element and the elastic contact element may be chosen such that the elastic contact element may be deformed to a predefined degree when a reservoir is accommodated in the cavity. In this compressed state the elastic contact element may exert a biasing force or pretensioning force in the longitudinal direction towards the reservoir and may thereby push the head or neck portion of the reservoir against the rigid bearing element. The reservoir may thus be secured or non-movably held in the longitudinal direction within the cavity of the housing of the drug delivery device.

The elastic properties of the elastic contact element may facilitate in damping and may serve to damp shocking movements or high acceleration impacts, for example, if the drug delivery devices drops to the floor. Furthermore, the elastic properties may be useful for the assembly of the first and second housing portions. The housing portions, for example, may be coupled to each other during assembly by plastic welding or bonding. In this case, the first and second housing portions may be pressed together by applying a holding force such that at least one housing portion may be elastically deformed in the longitudinal direction. After the welding or bonding process the holding force may be released or removed and the deformed housing portion may relax to its initial form. When the housing portion moves back after the welding or bonding process into its initial form the elastic contact element may compensate for the corresponding change in length of the cavity and may still be capable of exerting a pretensioning force that may be high enough to reliably hold the reservoir within the housing. Thus, the elastic contact element may help ensure that the reservoir is reliably and securably held within the module not only during the assembly but also during the entire life cycle of the drug delivery device.

The elastic contact element may be injection molded onto a surface of a body of the second housing portion. This may result in the number of parts that need to be handled and assembled being reduced since the elastic contact element may be non-releasably connected to, or integral with, the second housing portion. This may simplify the handling and assembly of the housing of the drug delivery device.

In the present context, the terms "substance", "drug", "medicament" and "medication" are to be understood to include any flowable medical formulation suitable for controlled administration through a means such as, for example, a cannula or a hollow needle, and may include a liquid, a solution, a gel or a fine suspension containing one or more medical active ingredients. A medicament may be a composition including a single active ingredient or a pre-mixed or co-formulated composition with more than one active ingredient present in a single container. Medication includes drugs such as peptides (e.g., insulin, insulin-containing drugs, GLP-1 containing drugs or derived or analogous preparations), proteins and hormones, active ingredients derived from, or harvested by, biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances.

The term "infusion system" refers to a drug delivery device with a cannula or needle that may remain in the skin of the patient for a prolonged period of time, for example several hours. By contrast, the term "injection system" or "injection device" is to be understood as a delivery device that may be removed from the injection site after each medication event or drug delivery process.

The infusion system may be, for example, a conventional medical drug pump such as an insulin pump with tubing or it may be a drug patch pump without tubing that may be attachable directly onto the skin of the user. The injection system may be, for example, a medication injection pen or a pen-shaped injection device.

The term "longitudinal", with or without "axis", refers to a direction or an axis through the device or components thereof in the direction of the longest extension of the device or the component. The terms "radial" refers to a direction through the device or components thereof in a direction generally perpendicular to the longitudinal direction.

The module may include a first and a second housing portion that may accommodate or enclose the reservoir in the assembled state. The first and second housing portions may define the module or the housing portions may form at least a portion of or an entire outer cover of the module. However, the term "housing" is not limited to an outermost element of the drug delivery device. For instance, the first and/or the second housing portion may form at least a part of the outer cover of the drug delivery device.

In implementations, the module may be a disposable module of the drug delivery device. The drug delivery device may include the aforementioned module, a reusable module, a second disposable module and/or additional modules, units or elements. For instance, the aforementioned module may form at least a portion of the drug delivery device.

The bearing element may be adapted to support, hold or abut a head or neck portion of the reservoir. For this, the bearing element may be provided in form of a curved or planar contact surface, a contact element or a flat portion within the first housing portion. The bearing element may be integrally formed with or be monolithic with the first housing portion. Alternatively, the bearing element may be formed as a separate member but may not be integrally formed with the first housing portion. In this case, the bearing element may be non-releasably connected or fixed to the first housing portion.

The elastic contact element may be adapted to support, hold or abut an end of the reservoir which may be opposite the head or neck portion. Thus the elastic contact element may support the rear end of the reservoir, which rear end may be furthest away from the outlet in the reservoir for dispensing the medication. For instance, the elastic contact element may be compressed in the longitudinal direction when the first and second housing portions are connected to each other to the assembled state when a reservoir is present within the cavity. The compressed elastic contact element may be adapted to exert a pretensioning force to the reservoir. Therefore, the head or neck portion of the reservoir may be pressed against the bearing element and thus the reservoir may be reliably non-movably held or secured within the cavity of the module.

In some implementations, the elastic contact element may support the reservoir only in the longitudinal direction such that the reservoir, e.g., the rear end of the reservoir (the end opposite the neck or head portion of the reservoir), may be, at least in a limited range, free to move in a plane perpendicular to the longitudinal direction.

The term "free of play" is to be understood that the reservoir cannot move within the module relative to the first and second housing portions in the longitudinal direction during normal use, e.g. during dose setting and dose dispensing. This does not exclude that the first or second housing portion may be slightly (up to several millimeters) deformed during the assembly process, for example, during connecting the first and second housing portions with each other.

During assembly or manufacture of the complete module of the drug delivery device, the first and second housing portions may be connected or attached to each other in the assembled state in which the first and second housing portions form a cavity for accommodating the reservoir. The connection between the first and second housing portions may be either releasable (for example by a snap-fit connection) or non-releasable (for example by an adhesive or by welding or bonding). After the first and second housing portions are connected to each other, a cavity may be formed, which may be adapted to accommodate the reservoir within the module. For example, the cavity may have essentially the shape of a cylinder, a rectangle or a polygon. For instance, in the assembled state the first and second housing portions may completely enclose the reservoir. Thus in the assembled state, the reservoir may not be accessed or removed from the module from the device.

The elastic contact element may be injection molded onto a surface of a body of the second housing portion. Thus, during the production of the second housing portion, the elastic contact element may be inextricably or non-releasably connected or firmly bonded to the body of the second housing portion but the elastic contact element may be made of a material different than the body of the second housing portion. For example, the elastic contact element may be essentially made of silicone, rubber or any thermoplastic elastomer, whereas the body of the second housing portion may be essentially made of rigid plastic, for example a thermoplastic.

The techniques used for the production of the second housing portion may lead to a component or a material referred to as dual-component material or two-component material (2K material). However, the second housing portion is not limited to being formed of only two different materials. The second housing portion may also made of three or more different materials. The body of the first and/or second housing portions may also made by injection molding. The elastic contact element may be injection molded, for example, in the same production step as the body of the second housing portion. Alternately, the elastic contact element may be injection molded in a separate production step. In this case the elastic contact element may be injection molded onto a previously produced body of the second housing portion.

In some implementations, the elastic contact element may be compressible in the longitudinal direction of the cavity. This may correspond to the longitudinal direction of the reservoir accommodated in the cavity. The compressible elastic contact element may thus be able to exert a pretensioning force against an end of the reservoir accommodated in the cavity such that the head or neck portion of the reservoir is pressed with the pretensioning force against the bearing element. For instance, the elastic contact element may only be compressible in the longitudinal direction such that the pretensioning force may be exclusively directed in the longitudinal direction.

In an alternative implementation the elastic contact element may be deformable in another direction, for example, in an inclined direction or in a plane perpendicular the longitudinal direction.

In some implementations, the elastic contact element may consist of, may be formed of or may include silicone or a thermoplastic elastomer (TPE), for example a rubber material. These materials may be well-suited for injection molding the elastic contact element onto the body, such as a plastic body, of the second housing portion.

Alternatively, the elastic element may be made of other injection moldable material, for example, thermoset plastic.

In some implementations, the body of the second housing portion may consist of, may be formed of or may include plastic material other than a thermoplastic elastomer, e.g., the second housing portion may be free of a thermoplastic elastomer. For example, such materials may be a common thermoplastic, a thermoset plastic, a non-elastomer thermoplastic, a metal or a composite material.

If the elastic contact element is made of a thermoplastic elastomer and the body is made of metal or a composite material, the complete second housing portion may be a so-called hybrid material. This may enable suitable material properties from plastics and from metals to be used in combination.

In some implementations, the second housing portion may include at least two elastic contact elements which support the rear end of the reservoir which may be the end of the reservoir opposite the neck or head portion end of the reservoir. The reservoir may be supported stably with one or more elastic contact elements, such as with two or more elastic contact elements. The elastic contact elements may be injection molded onto the body of the second housing portion and the contact elements may be circumferentially arranged along a rim portion of the accommodated reservoir.

Alternately, the second housing portion may include only one elastic contact element, and the contact element may, for example, be ring-shaped for supporting a rear end of the reservoir.

In some implementations, the elastic contact element may have an elongated form, which may extend in the longitudinal direction of the cavity. The elongated form may allow for optimal compression of the contact element.

In some implementations, the elastic contact element may be cone-shaped. The portion of the cone with the larger diameter may contact the body of the second housing portion and the free end of the cone may extends away from the body in the longitudinal direction towards the bearing element. The cone-shaped elastic contact element may allow for more exactly specifying and predetermining the force generated by the compression of the elastic contact element. Namely, the contact element may be configured such that the force generated due to compression is progressive with respect to the degree of compression. This may facilitate configuring or defining the pretensioning force of the elastic contact element for holding the reservoir within the module.

In some implementations, the bearing element may be formed by a rigid plastic. Such a rigid plastic may not be elastically deformable. Even if nearly all material can be minimally deformed before a plastic deformation occurs (i.e., Hooke's law) the term "rigid" is to be understood that no essential elastic deformation occurs. An example of a rigid plastic is a common thermoplastic. In contrast to a rigid plastic, an elastomer is elastically deformable.

The first housing portion may include, on an interior of the housing portion, guiding means or a guiding structure for supporting the reservoir in a radial direction, which is perpendicular to the longitudinal direction. The guiding means may be inner walls, radial ribs, cams or protrusions extending within the housing portion. The guiding means may support the reservoir if the first housing portion is deformed in the longitudinal direction, for example during a welding or bonding process. Hence, an undesirable tilted position of the reservoir may be prevented by the guiding means.

In some implementations, the first or the second housing portion may include a blind hole or bore for accommodating the reservoir. The other of the first or second housing portions may be formed as a cover or may include a cover for at least partially closing an inlet of the blind hole. The blind hole and the cover may form the cavity for the reservoir. Thus, the reservoir may be accommodated or enclosed by the first and the second housing portions. The cover may include an opening for a plunger rod such that the plunger rod runs through the cover to the plunger within the reservoir. When moving the plunger rod in a dispensing direction the plunger rod may move the plunger to the dispensing end within the reservoir and thus may push the substance or medication out of the reservoir.

The assembly with a blind hole and a cover may simplify assembly of the reservoir and the module.

In the assembled state, the first and second housing portions may be connected to each other by welding, such as by plastic welding, for instance when the housing portions are made of or essentially made of plastic. Therefore, the first and second housing portions may be non-releasably connected or attached to each other. A connection of the first and second housing portions by welding may be easily implemented and may allow the module to be economically produced.

Alternatively, the first and second housing portions may be connected to each other by adhesive, by screws, by rivet joints or by a snap-fit connection.

In some implementations, the drug delivery device may be an infusion device, such as an infusion drug pump. The infusion device may include a dose and dispensing mechanism with a plunger rod. The plunger rod may be adapted to move the plunger within the reservoir for dispensing the medication in the reservoir.

In some implementations, the infusion device may be a patch pump and may include a disposable part and a reusable part. For instance, the disposable part may include the module according to the present disclosure. The reusable part may include the dose and dispensing mechanism.

Implementations further relate to a drug delivery device including the reservoir. The reservoir may also be referred to as a cartridge, a carpule or a container.

In further implementations, the reservoir may include a nut, a cavity or a depression at an end opposite the neck or head portion of the reservoir for at least partially accommodating the elastic contact element in the assembled state.

BRIEF DESCRIPTION OF THE DRAWINGS

The subject matter of the present disclosure will be explained in more detail in the following text with reference to the disclosed implementations, which are illustrated in the attached drawings, in which.

The reference symbols used in the drawings, and their primary meanings, are listed in summary form in the list of reference elements. In principle, identical parts are provided with the same reference symbols in the figures.

DETAILED DESCRIPTION

Figure 1:
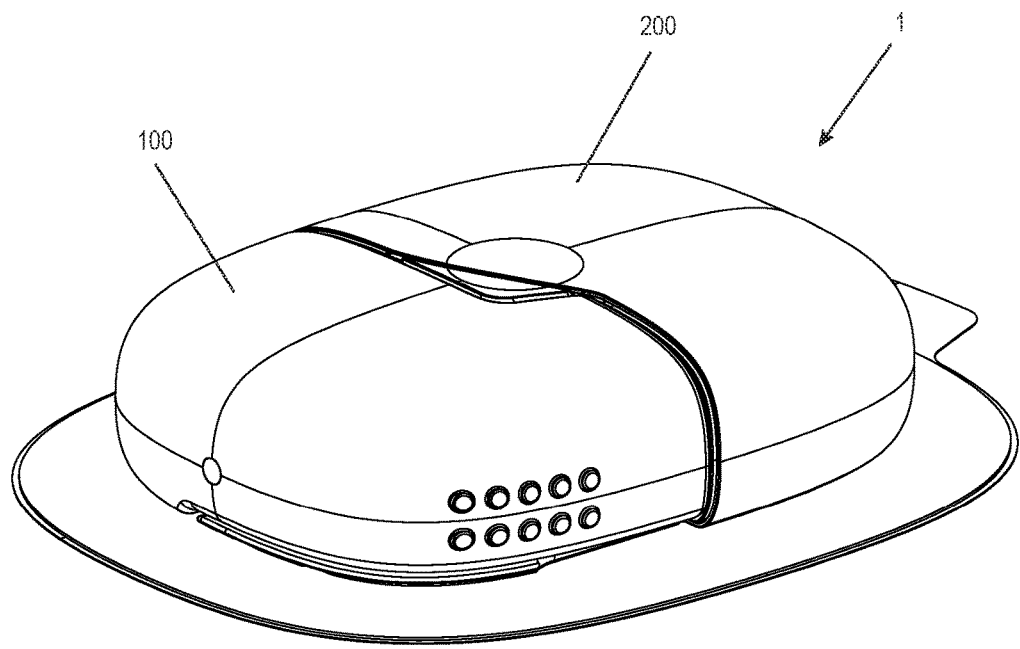
FIG. 1 depicts a perspective view of a patch pump.

FIG. 1 depicts an isometric view of a drug delivery device according to the present disclosure. The drug delivery device may be provided as an infusion patch pump 1. The patch pump 1 may include a reusable pump unit 100 and a disposable reservoir unit 200. The reservoir unit 200 may include a reservoir 210 (FIG. 2) for storing a medication and a needle assembly 220 fluidly connected to the reservoir 210 to deliver medication from the reservoir 210 into the body of a patient. At the bottom of the reservoir unit 200 an adhesive patch assembly 280 (FIG. 2) may be provided for attaching the patch pump 1 to the body of the patient. The pump unit 100 may be releasably and sealingly connected to the reservoir unit 200 by a bayonet connection. FIG. 1 shows the complete patch pump 1 with both the pump unit 100 and the disposable reservoir unit 200 connected to each other.

In view of the aforementioned description of the drug delivery device configured as an infusion patch pump 1, the user may only be provided with two components for assembly: the reusable pump unit 100 with all of its components intended for multiple uses or for continuous use, and the disposable reservoir unit 200 with all of its components intended for single use.

Figure 2:
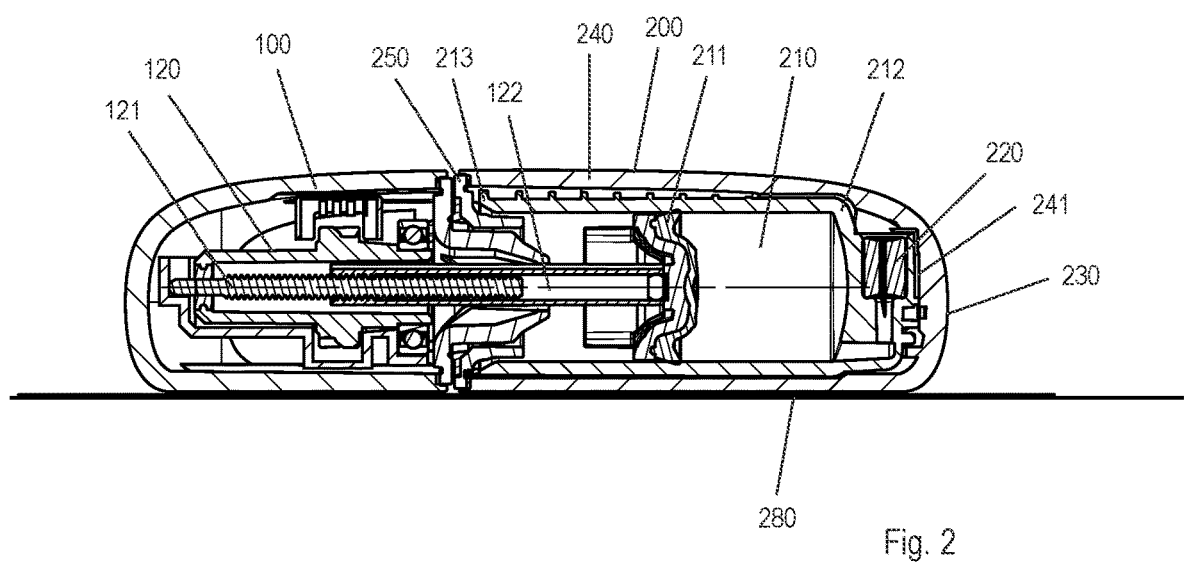
FIG. 2 depicts a cross-section side view of the patch pump of FIG. 1, in which the cross-section is taken parallel to a longitudinal axis at the center of the of the patch pump.

FIG. 2 depicts a cross-sectional view of the patch pump of FIG. 1, where the cross-section runs along a middle of the patch pump 1 along the longitudinal axis of the patch pump 1. The pump unit 100 may include a drive mechanism 120 for driving a plunger rod 122, an encoder (e.g., CPU or processor) to track the movement of the drive mechanism 120, a rechargeable battery and programmable electronic system control circuitry configured to control the set-up, drug delivery and tracking of the patch pump 1. The battery may be rechargeable by a further battery arranged in the disposable reservoir unit 200, while the drive mechanism 120 may be coupleable to the reservoir unit 200.

The drive mechanism 120 may operate mechanically from a threaded rod 121 via plunger rod 122 on a plunger 211 in the reservoir 210 to dispense the medication out of the reservoir 210. The needle assembly 220 within the reservoir unit 200 may provide a fluid connection from the reservoir 210 to the exterior of the patch pump 1 for medication delivery to the patient.

The reservoir unit 200 may include a module 230 made of plastic. The module 230 may include a main portion 240 and a cover portion 250. The main portion 240 may include a blind hole for accommodating the reservoir 210 and the cover portion 250 may cover an opening of the blind hole. In other words, the main portion 240 and the cover portion 250 may form a cavity or space for accommodating the reservoir 210, and the reservoir 210 may thus be enclosed by the main portion 240 and the cover portion 250 of the module 230.

The reservoir 210 may include a dispensing end 212 where the needle assembly 220 may be arranged. The dispensing end 212 may abut against a rigid bearing surface 241 of the main portion 240 and a rear end 213 of the reservoir 210 opposite the dispensing end 212 may abut elastic contact elements 251 (see FIGS. 4 and 5) of the cover portion 250. In contrast to the elastic contact elements 251, the dispensing end 212 of the reservoir 210 may be rigidly supported by the bearing surface 241 of the main portion 240, which may not be elastically deformable. The rear end 213 of the reservoir 210 may be supported by the elastically deformable contact elements 251. As described in detail herein the reservoir 210 may be non-movably secured or be free of play secured between the bearing surface 241 of the main portion 240 and the elastic contact elements 251 of the cover portion 250 (shown in FIGS. 4 and 5).

Figure 3:
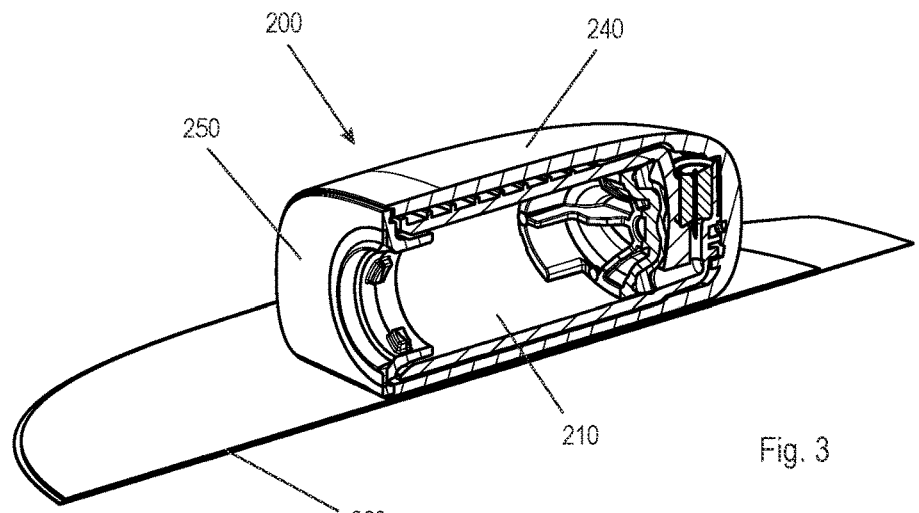
FIG. 3 depicts an isometric cross-section view of a reservoir unit of the patch pump of FIG. 1 taken along the longitudinal axis of the patch pump.

FIG. 3 shows an isometric, cross-section view of the reservoir unit 200 of the patch pump 1 detached and separated from the pump unit 100, where the cross-section runs along a middle of the patch pump 1 along the longitudinal axis of the patch pump 1. As it can be seen in FIG. 3 the reservoir unit 200 may include the adhesive patch assembly 280 at the bottom of the module 230 towards the body of the user or patient. FIG. 3 shows the reservoir unit 200 in an assembled state in that the main portion 240 and the cover portion 250 of the module 230 are connected to each other.

Figure 4:
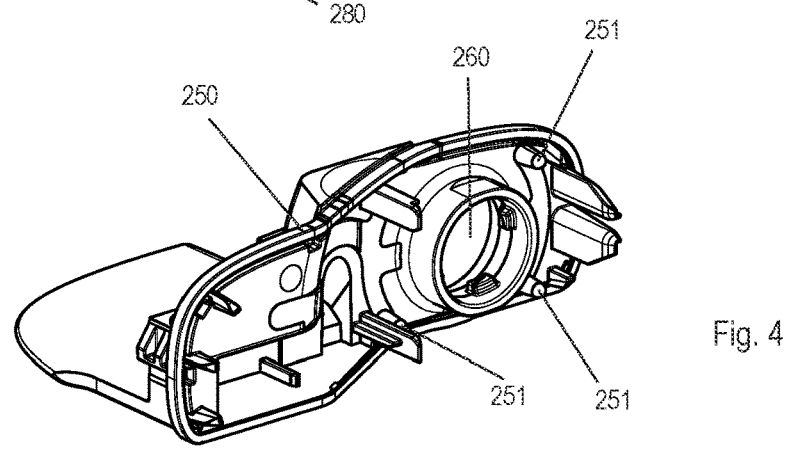
FIG. 4 depicts an isometric view of a cover portion of a housing of the reservoir unit of the patch pump of FIG. 1.

FIG. 4 depicts a perspective view of the cover portion 250 of the module 230 of the reservoir unit 200. The cover portion 250 may be adapted to be non-releasably or non-detachably connected to the main portion 240, and the body of the cover portion 250 may be made of a thermoplastic. The elastic contact elements 251 may be provided in the form of four cone-shaped protrusions and may be circumferentially arranged around an opening 260 defined in the cover portion 250. The contact elements 251 may be injection molded onto the body of the cover portion 250 and may be made of silicone or thermoplastic elastomer.

Figure 5:
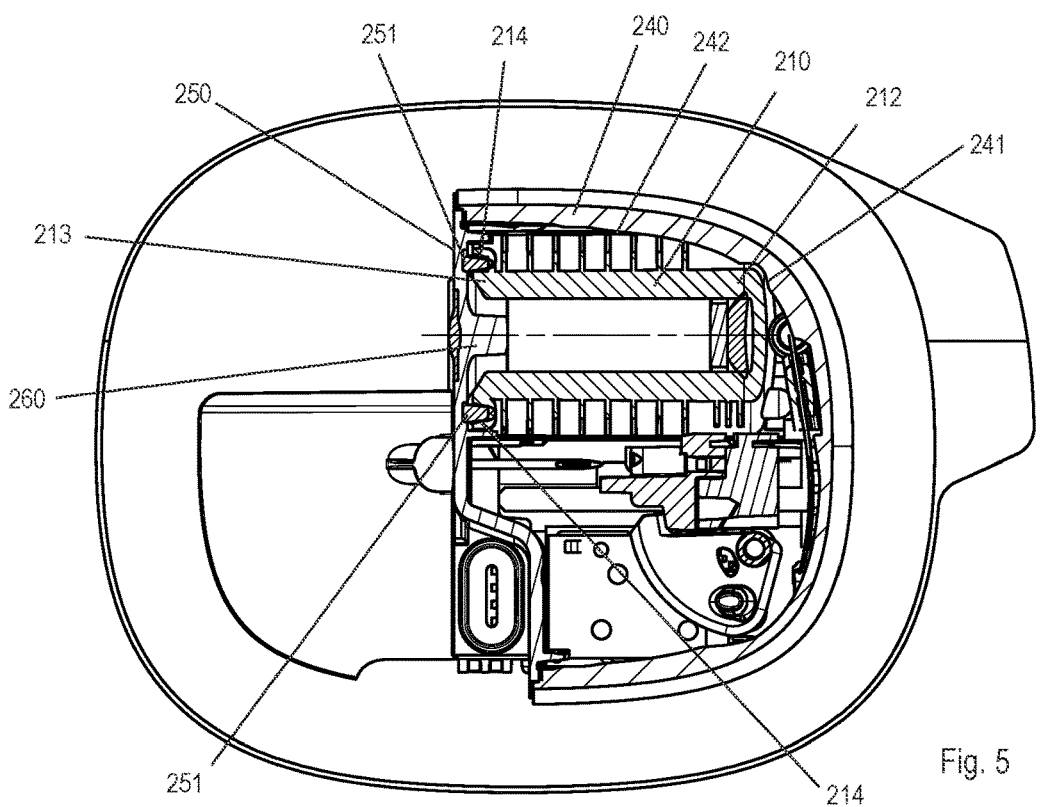
FIG. 5 depicts a cross-section top view of the reservoir unit in which the cross-section is taken perpendicular to the longitudinal axis of the patch pump without a top cover of the reservoir unit.

In FIG. 5 a top view of the reservoir unit 200 is depicted as a cross-section view (outer housing on top not shown) illustrating the interior of the reservoir unit 200 taken along a line perpendicular to the longitudinal axis of the patch pump 1. The reservoir unit 200 depicted in FIG. 5 is slightly enlarged compared to FIGS. 3 and 4. In FIG. 5, it can be seen that the cone-shaped elastic contact elements 251 may protrude in the longitudinal direction of the patch pump 1 and may be accommodated in corresponding depressions 214 in the rear end 213 or rim portion of the reservoir 210.

During assembly, the reservoir 210 may be first inserted into the blind hole of the main portion 240 such that the dispensing end 212 of the reservoir 210 abuts the bearing surface 241 of the main portion 240. Subsequently, the cover portion 250 may be connected to the main portion 240 portion by plastic welding or bonding to cover the blind hole. During this connection process the cover portion 250 may be pressed onto the main portion 240 and may thereby deform (compress) the main portion 240 in the longitudinal direction. Upon termination of the connecting process the pressure on the cover and main portion 240, 250 may be released and the main portion 240 may relax into its initial shape. During this relaxing movement of the main portion 240 the reservoir 210 may be radially guided by inner side walls 242 of the main portion 240. The reservoir may include ribs that may slide along the inner side walls 242 to prevent the reservoir 210 from moving into a blocked or tilted position during deformation of the main portion 240.

Due to the elastic deformability of the elastic contact elements 251 in the longitudinal direction, the reservoir 210 may be secured and may be free of play during the connection process (e.g., via welding or bonding) as well as after relaxation of the housing portions 240, 250, such as during normal use of the drug delivery device. The configuration of the main portion 240 and the configuration of the elastic contact elements 251 may be selected such that the elastic contact elements 251 are continuously at least slightly elastically deformed (e.g., compressed) even after relaxation of the main portion 240. Therefore, the elastic contact elements 251 may compensate for a varying length between the supporting points in the longitudinal direction, namely between the elastic contact elements 251 and the bearing surface 241. Thus, the compressed elastic contact elements 251 may continuously exert a pretensioning force on the rear end 213 of the reservoir 210 and may thus press the reservoir 210 against the bearing surface 241. The dispensing end 212 of the reservoir 210 may be rigidly supported by the bearing surface 241 of the main portion. This may enable an increasing force acting in the longitudinal direction towards the dispensing end to be detected. Such an increasing force may occur, for example, during an occlusion. Due to the pretensioning force, the reservoir 210 may not move within the cavity and may be secured free of play, which may allow for a reliable and precise dosing and dispensing of the medication.

In a second implementation, the module 230 according to the present disclosure may be implemented in a normal infusion pump including tubing. In this second implementation, all features and functions described herein relating to the module 230 with the main portion 240 and the cover portion 250 including the elastic contact elements 251 apply in the same manner. The module 230 according to the present disclosure may be implemented without restriction even for an injection system.

While the implementations have been described in detail in the drawings and foregoing description, such description is to be considered illustrative or exemplary and not restrictive. Variations to the disclosed embodiments will be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. The mere fact that certain elements or steps are recited in distinct claims does not indicate that a combination of these elements or steps cannot be used to advantage, specifically, in addition to the actual claim dependency, any further meaningful claim combination shall be considered disclosed.

LIST OF REFERENCE ELEMENTS 1 patch pump
100 pump unit
120 drive mechanism
121 threaded rod
122 plunger rod
200 reservoir unit
210 reservoir
211 plunger
212 dispensing end
213 rear end
214 depression
220 needle assembly
230 module
240 main portion
241 bearing surface
242 side wall
250 cover portion
251 elastic contact elements
260 opening
280 patch assembly

What is claimed is:

1. A drug delivery device comprising a module adapted to accommodate a reservoir configured for holding a liquid drug, wherein the module comprises:
   a first housing portion, the first housing portion comprising a bearing element configured for supporting a neck or head portion at a first end of the reservoir; and
   a second housing portion, the second housing portion comprising an elastic contact element configured for supporting a second end of the reservoir opposite the first end of the reservoir,
   wherein the first and second housing portions are configured to be connected to one another in an assembled state in which the first and second housing portions form a cavity for accommodating the reservoir, wherein the bearing element and the elastic contact element each define a limiting structure of the cavity in a longitudinal direction of the cavity, which together are configured to secure or hold the reservoir free of play within the cavity, wherein the elastic contact element is injection molded onto a surface of a body of the second housing portion, and wherein the elastic contact element is made from a material that differs from a material from which the body is made.

2. The device according to claim 1, wherein the elastic contact element is configured to be compressible in the longitudinal direction of the cavity.

3. The device according to claim 1, wherein the elastic contact element comprises a thermoplastic elastomer or silicone.

4. The device according to claim 1, wherein the body of the second housing portion is made of plastic material.

5. The device according to claim 1, wherein the second housing portion comprises at least two elastic contact elements.

6. The device according to claim 1, wherein the elastic contact element is elongated and extends in the longitudinal direction of the cavity.

7. The device according to claim 1, wherein the elastic contact element is cone-shaped.

8. The device according to claim 1, wherein the bearing element is formed by a thermoplastic.

9. The device according to claim 1, wherein an interior of the first housing portion comprises a sidewall configured for guiding and supporting the reservoir in a direction perpendicular to the longitudinal direction.

10. The device according to claim 1, wherein one of the first or second housing portions defines a blind hole configured for accommodating the reservoir, and an other of the first or second housing portions defines a cover configured for at least partially closing an inlet of the blind hole.

11. The device according to claim 10, wherein the second housing portion defines the cover, wherein at least two elastic contact elements are provided by the second housing portion, wherein each of the elastic contact elements is elongated and extends in the longitudinal direction of the cavity.

12. The device according to claim 11, wherein the reservoir comprises at least two nuts or depressions at the second end of the reservoir, each configured for accommodating one of the at least two elastic contact elements, wherein each elastic contact element presses the reservoir in the longitudinal direction of the cavity against the bearing element such that the reservoir is secured or held free of play within the cavity.

13. The device according to claim 1, wherein in the assembled state, the first and second housing portions are connected to each other by a welding or bonding connection.

14. The device according to claim 1, wherein the drug delivery device is configured as an infusion device.

15. The device according to claim 1, wherein the reservoir comprises a nut or a depression at the second end of the reservoir configured for accommodating the elastic contact element in the assembled state.

16. A module adapted for use with a drug delivery device, the module adapted to accommodate a reservoir for holding a liquid drug, wherein the module comprises:

a first housing portion, the first housing portion comprising a bearing element configured for supporting a neck or head portion at a first end of the reservoir; and a second housing portion, the second housing portion comprising an elastic contact element configured for supporting a second end of the reservoir opposite the first end of the reservoir, wherein the first and second housing portions are configured to be connected to each other in an assembled state in which the first and second housing portions form a cavity for accommodating the reservoir, wherein the bearing element and the elastic contact element each define a limiting structure of the cavity in a longitudinal direction of the cavity, which together are configured to secure or hold the reservoir free of play within the cavity, wherein the elastic contact element is injection molded onto a surface of a body of the second housing portion, and wherein the elastic contact element is made from a material that differs from a material from which the body is made.

17. The device according to claim 16, wherein the elastic contact element is elongated and extends in the longitudinal direction of the cavity, and wherein the contact element presses the reservoir in the longitudinal direction of the cavity against the bearing element such that the reservoir is secured or held free of play within the cavity.

18. A module adapted to accommodate a reservoir configured for holding a liquid drug and adapted to couple to a drive mechanism for dispensing the drug from the reservoir, wherein the module comprises:

a first housing portion, the first housing portion comprising a bearing element configured for supporting a neck or head portion at a first end of the reservoir; and a second housing portion, the second housing portion comprising an elastic contact element configured for supporting a second end of the reservoir opposite the first end of the reservoir, wherein the first and second housing portions are configured to be connected to one another in an assembled state in which the first and second housing portions form a cavity for accommodating the reservoir, wherein the bearing element and the elastic contact element each define a limiting structure of the cavity in a longitudinal direction of the cavity, which together are configured to secure or hold the reservoir free of play within the cavity, wherein the elastic contact element is injection molded onto a surface of a body of the second housing portion, and wherein the elastic contact element is made from a material that differs from a material from which the body is made.

19. The module of claim 18, wherein the elastic contact element is elongated and extends in the longitudinal direction of the cavity, and wherein the contact element presses the reservoir in the longitudinal direction of the cavity against the bearing element such that the reservoir is secured or held free of play within the cavity.

20. The module of claim 18, wherein the second housing portion defines a cover of the module, wherein the cover is configured to receive at least a portion of the drive mechanism.

* * * * *